United States Patent [19]

Stout

[11] 4,414,324

[45] * Nov. 8, 1983

[54] IMMUNOASSAY METHOD AND APPARATUS

[75] Inventor: Robert L. Stout, Overland Park, Kans.

[73] Assignee: BMA Laboratory Services, Inc., Kansas City, Mo.

[ * ] Notice: The portion of the term of this patent subsequent to May 12, 1998 has been disclaimed.

[21] Appl. No.: 252,427

[22] Filed: Apr. 9, 1981

Related U.S. Application Data

[63] Continuation of Ser. No. 40,641, May 21, 1979, Pat. No. 4,267,270.

[51] Int. Cl.³ .............................................. G01N 33/54
[52] U.S. Cl. ........................................ 435/7; 435/810; 436/518; 436/528; 436/538; 436/808
[58] Field of Search ........................ 435/7, 805, 810; 23/230 B; 424/1, 8, 12; 260/112 R, 121; 422/57; 436/518, 528, 538, 808, 810

[56] References Cited

U.S. PATENT DOCUMENTS

| | | | |
|---|---|---|---|
| 3,790,663 | 2/1974 | Garrison et al. | 424/1 |
| 3,904,367 | 9/1975 | Golibersuch | 424/1 |
| 3,932,141 | 1/1976 | Beall et al. | 23/230 B |
| 3,960,489 | 6/1976 | Giaver | 23/230 B |
| 3,966,556 | 6/1976 | Rubenstein et al. | 435/7 |
| 4,001,583 | 1/1977 | Barrett | 424/12 |
| 4,016,043 | 4/1977 | Schuurs et al. | 435/7 |
| 4,066,512 | 1/1978 | Lai et al. | 435/177 |
| 4,066,744 | 1/1978 | Price et al. | 435/7 |
| 4,067,959 | 1/1978 | Bolz | 23/230 B |
| 4,069,352 | 1/1978 | Parsons | 435/7 |
| 4,070,246 | 1/1978 | Kennedy et al. | 435/7 |
| 4,092,116 | 5/1978 | Giaver | 23/230 B |
| 4,157,280 | 6/1979 | Halbert et al. | 23/230 B |
| 4,166,844 | 9/1979 | Tu | 435/7 |
| 4,267,270 | 5/1981 | Stout | 435/177 |
| 4,352,884 | 10/1982 | Nakashima et al. | 435/7 |
| 4,357,142 | 11/1982 | Schall et al. | 435/7 |
| 4,363,634 | 12/1982 | Schall | 435/7 |

*Primary Examiner*—Thomas G. Wiseman
*Attorney, Agent, or Firm*—Schmidt, Johnson, Hovey & Williams

[57] ABSTRACT

An improved immunoassay sample determination process for determining the presence of a component of an antigen-antibody reaction in a sample is disclosed which substantially eliminates non-specific interactions between the sample and the reaction vessel wall surfaces during the antigen-antibody reaction, to thereby greatly increase the accuracy of the process. In practice, a site-deactivating medium such as an animal- or vegetable-derived total biological fluid or extract (e.g., plasma or gelatin) is covalently bound to the vessel wall surfaces for deactivation purposes. In preferred forms the process is solid-state, wherein one of the components of the antigen-antibody reaction is coupled covalently to the coating medium, and a reaction mixture fraction including the sample being determined and the other component which has been labeled, for instance by means of a colorimetrically active enzyme.

18 Claims, No Drawings

IMMUNOASSAY METHOD AND APPARATUS

This is a continuation of application Ser. No. 06/040,641, filed on May 21, 1979, U.S. Pat. No. 4,267,270.

BACKGROUND OF THE INVENTION

1. Field of the Invention

The present invention is broadly concerned with improved immunoassay processes wherein use is made of a site-deactivating medium for reducing or substantially eliminating non-specific interactions between a sample being tested and the surfaces of the reaction vessel. More particularly, it is concerned with an improved method of this type wherein the vessel wall surfaces in contact with the sample and antigen-antibody components during the reaction are coated and covalently bound with a medium such as a total biological fluid or extract for site-deactivation purposes.

2. Description of the Prior Art

A number of immunoassay techniques have been proposed in the past for determining, either qualitatively or quantitatively, the presence of a component of an antigen-antibody reaction in a given sample. For example, immunodiffusion and immuno-electrophoresis, complement fixation, passive hemagglutination and radio-immunoassay procedures have been developed. Furthermore, U.S. Pat. No. 3,654,090 describes a immunochemical assay process wherein use is of a component of an antigen-antibody reaction in insolubilized form, whereas the other component is covalently linked to an enzyme. The insolubilized and free enzyme-labeled components are added to a sample to be determined, and the antigen-antibody reaction is allowed to proceed to completion. If the sample contains one of the components of the antigen-antibody reaction, this component competes with the corresponding added component for reaction with the other component of the reaction. When the antigen-antibody reaction is complete, the insolubilized and free fractions are separated, and the activity of the labeled component is determined by an appropriate measure of one of the separated fractions.

Solid-state techniques analogous to that outlined above are in widespread use. In such processes, one of the components of an antigen-antibody reaction is adsorbed onto an insoluble carrier or surface in a reaction vessel; for example, the component can simply be adsorbed directly to the wall surfaces of a synthetic resin vessel. A reaction mixture fraction is then added to the vessel which would include the sample being determined and the other component of the antigen-antibody reaction which has been labeled. Such labeling can be accomplished by a number of means, for example using a radioisotope or covalently linking an enzyme to the free component. The antigen-antibody reaction is then allowed to proceed, wherein one of the following possibilities can occur: (1) If the sample being determined is free of the labeled component, then all of the latter will react with the insolubilized fraction, and the remaining reaction mixture fraction will be free of antigen; or (2) If the sample contains a quantity of the component corresponding to the labeled component, a competition results between the labeled component and that in the sample. In this case, because of such competition, an amount of the labeled component will remain in the reaction mixture fraction. In either event, the remainder of the reaction mixture fraction and the insolubilized fractions are separated, and the label activity is measured on one of these fractions. Determination of activity of course depends on the nature of the label; in the case of a radioisotope, an isotope counter is employed, whereas if an enzyme label is employed, enzyme activity may be determined colorimetrically.

While the above described solid-state assay procedures are known, a persistent problem which has detracted from the usefulness thereof involves non-specific interaction which can occur between components of the sample and the reaction vessel wall surfaces and/or other adsorption surfaces present during the antigen-antibody reaction. As can be appreciated, such non-specific interaction can materially detract from the accuracy of the solid-state technique, particularly if quantitative determinations are desired.

To give but one example of this problem, many insurance companies today require a urine sample from applicants for their policies, and such samples are often checked for the presence of thiazides therein. If such thiazides are present, a good indication is given as to whether the applicant is taking certain types of medications. In any event, use of the above-described solid-state technique in connection with thiazide determinations presents significant problems relating to non-specific interactions, which is enhanced because of varying quantities of urea present in the urine samples. In fact, such interactions can be so significant as to lead to totally erroneous qualitative results, i.e., a urine sample free of thiazide tests as a positive, or a thiazide-containing sample tests as a negative.

There is therefore a decided need in the art for an improved immunochemical assay process which overcomes the problems associated with non-specific interactions, particularly in the case of solid-state immunoassay techniques.

DESCRIPTION OF THE PREFERRED EMBODIMENT

The present invention is concerned with a process for the determination of the presence of a component of an antigen-antibody reaction in a sample. In its particular aspects, the invention contemplates the use of a site-deactivating medium in the process for the purpose of eliminating or at least substantially minimizing non-specific interactions between the sample being tested and the defining walls of the reaction vessel and/or other possible adsorption surfaces therein.

In accordance with the invention, respective, calculated quantities of the antigen component and the antibody component of the reaction are provided, with one of the components being labeled.

It is to be understood that analogues of tested for compounds may be used in this context, as long as the analogue and the compound being tested for have comparable biological activities. To give but one example, in a test for the presence of a thiazide antigen in a urine sample, a thiazide analogue antigen and corresponding antibody can be used. As used herein, the step of providing antigen and/or antibody components of a given reaction shall be taken to include provision of such biologically similar analogues.

Either the antigen or antibody component can be labeled, but preferably the antibody is labeled. Likewise, a variety of labels can be employed, such as a radioactive isotope or a color-active enzyme; in preferred forms, a color-active enzyme is preferred.

In addition, a reaction vessel is provided which is defined by wall surfaces which will contact the reactants and sample employed in the test procedure. A multiple-well microtiter plate is advantageously used as the reaction vessel, especially in conjunction with screening tests for a large number of samples. In this case, the defining walls of the respective wells can present interference problems, as will be explained in detail hereinafter.

In the process, the defining wall surfaces of the plate wells are coated by covalently bonding thereto a site-deactivating medium which serves, during the antigen-antibody reaction, to minimize non-specific interactions between these surfaces and the sample being tested. The site-deactivating medium is selected from the group consisting of animal-derived total biological fluids, and extracts thereof, vegetable-derived total biological fluids, and extracts thereof, and mixtures of any of the foregoing. Preferably, the medium should be water soluble so as to facilitate the covalent bonding thereof to the surface or surfaces.

One of the provided antigen or antibody components is insolubilized, most preferably by covalently bonding the selected component directly to the site-deactivating medium. Preferably, the antigen component of the reaction is insolubilized.

The next step involves adding a reaction mixture fraction to the vessel which includes the sample being tested and the noninsolubilized component which has been provided. In the preferred process, the noninsolubilized component would be the antibody, and this antibody would in turn be the component which had been labeled.

The antigen-antibody reaction is then allowed to proceed to completion in the vessel. As described above, there are two possibilities in connection with this reaction. That is to say, if the sample being tested does not contain the tested for component of the antigen-antibody reaction, all of the provided antigen and antibody will react. On the other hand, if the sample contains the tested for component, a competition will result for reaction with the remaining component. In the case of the preferred process wherein the antigen is insolubilized and a labeled, soluble (i.e., noninsolubilized) antibody is placed in the reaction vessel along with the sample, the following can occur. If the sample contains the antigen being tested for, there will be a competition between the antigen within the sample and the insolubilized antigen for reaction with the labeled antibody. If none of the antigen being tested for is present, all of the labeled antibody will react with the insolubilized antigen.

The final steps of the process involve separating whatever remains of the reaction mixture fraction from the insolubilized fraction and whatever has reacted with the latter, followed by determining whether the tested for component of the antigen-antibody reaction is present in the sample by determining the activity of the labeled component in one of the separated fractions. Again referring to the most preferred process, the determination procedure involves contacting a color-activating material with the insolubilized fraction and whatever has reacted with the latter. If no tested for antigen is present in the sample, a first color reaction will obtain because of the fact that all of the labeled antibody has reacted with the insolubilized antigen. If the sample contains the tested for antigen, less of the labeled antibody will have reacted with the insolubilized antigen (by virtue of the competition for reaction with the antigen between the labeled antibody and the antigen in the sample), and therefore a different amount of color reaction will obtain.

The most preferred labeling enzyme is horseradish peroxidase, whereas the most preferred site-deactivating medium is selected from the group consisting of animal-derived plasma, animal-derived sera, vegetable-derived gelatins, and mixtures of the foregoing.

The following example will illustrate in detail a process in accordance with the invention. It is to be understood however, that the example is for illustrative purposes only, and nothing therein should be taken as a limitation upon the overall scope of the invention.

EXAMPLE

The present invention is eminently suited for large scale determination of the presence of thiazides in human urine samples. In a representative procedure, multiple-well synthetic resin microtiter plates are employed which serve as reaction vessels; and the defining walls of the respective wells also present insolubilizing surfaces used in the determination. Moreover, a thiazide analogue is used as the antigen, and a thiazide antibody covalently linked to horseradish peroxidase (HRP) enzyme is used as the labeled antibody.

The HRP-labeled antibody is made as follows. A quantity of the antigen analogue, 3-($\beta$-carboxyethyl)-6-chloro-7-sulfamoyl-1,2,4-benzothiadiazine-1,1-dioxide (see U.S. Pat. No. 3,287,360) is reacted with bovine serum albumin (BSA), using 64.5 mg. of the thiazide compound and 200 mg. of BSA in 8 ml. distilled water. 40 mg. of EDAC, i.e., 1-ethyl-3(3-dimethylaminopropyl)carbodiimide), is added to the mixture and the latter is allowed to incubate overnight. The pH of the mixture is maintained between 5.5 and 6.

The incubated material is then dialyzed against distilled water for 3 days. This material is then mixed with Freund's complete adjuvant and injected at multiple sites on the dorsal lateral surface of four goats. Two of the goats developed the appropriate antibody, which was recovered by conventional means.

In plate preparative procedures, a commercially available Cooke microtiter plate is first washed with deionized water and air dried. The plate wells are then coated with a site-deactivating medium, in this case goat plasma. Whole goat plasma is first diluted 1:20 (V:V) with a 0.1 Molar phosphate buffered saline (PBS) solution (pH7) containing 0.05 Molar urea. Five milligrams of EDAC per milliliter is next added to the diluted goat plasma, and 200 $\mu$l of the final mixture is added to each plate well. The plate is then incubated overnight at room temperature, whereupon it is decanted and washed six times with deionized water.

The propionic acid analogue of thiazide, 3-($\beta$-carboxyethyl)-6-chloro-7-sulfamoyl-1,2,4-benzothiadiazine-1,1-dioxide, (the antigen of the antigen-antibody reaction) is then covalently coupled to the goat plasma coating. This is accomplished by adding to each plate well 200 $\mu$l of a solution of 5 mg. of EDAC and 0.25 mg of the thiazide analog per milliliter of the phosphate buffered saline solutions. The plate is then incubated overnight at room temperature. Following incubation, the plate is decanted and washed six times with deionized water. The plate may be stored wet or dry.

In testing procedures a reaction mixture comprising a sample fraction of 25 $\mu$l of test urine and two hundred $\mu$l of the horseradish peroxidase (HRP) labeled antithiazide antibody in PBS is added to each well. The mixture is then agitated to insure proper mixing, and allowed to react at room temperature for about 20 minutes.

The respective reaction mixtures are then dumped, and the plate is washed six times with deionized water and shaken dry. Three hundred microliters of a known color-generating substance, 0.018 Molar ABTS (2,2'-azino-di-(3-ethyl-benzythiazoline sulfonic acid) diammonium salt) and 1.0 micromolar $H_2O_2$ in 0.1 M phosphate (pH 6), is added to each plate well. The plate is then incubated at room temperature and is read by visual observation for the presence or lack of color. Positives (thiazides present) are colorless to light green, whereas negatives (no thiazides present) will be dark green in color.

Having thus described the invention, what is claimed as new and desired to be secured by Letters Patent is:

1. In an assay process for the determination of an immunochemical component in a sample, wherein the sample, a first immunochemical component and a second immunochemical component are immunochemically incubated in a vessel, one of said first and second components being insolubilized in said vessel, one of said first and second components being labeled, said first and second components each having a specific immunochemical affinity for another component in said vessel, or for said component to be determined, during said incubation thereof, the insolubilized component is separated from the remainder of the reaction mixture, and it is thereafter determined whether said sample contained said component to be determined, the improvement which comprises:
   covalently bonding to the walls of said vessel a site-deactivating medium for minimizing nonspecific interactions, said insolubilized component being covalently attached to said medium, and
   said medium being selected from the group consisting of water soluble animal-derived plasma, animal-derived sera, vegetable-derived gelatins and mixtures thereof.

2. The process as set forth in claim 1, wherein said immunochemical component to be determined is an antigen.

3. The process as set forth in claim 1, wherein said labeled immunochemical component is an antibody.

4. The process as set forth in claim 1, wherein the label of said immunochemical component is an enzyme.

5. The process as set forth in claim 1, said enzyme being horseradish peroxidase.

6. The process as set forth in claim 1, said component-determining step comprising determining the activity of the labeled component.

7. The process as set forth in claim 1, said determination being performed colorimetrically.

8. The process as set forth in claim 1, said component to be determined being a thiazide antigen.

9. The process as set forth in claim 1, wherein said first component is covalently coupled to said medium, said sample and labeled immunochemical component being thereafter simultaneously placed in said vessel.

10. The process as set forth in claim 1, said first immunochemical component being an analogue of said component to be determined.

11. A system for determining the presence of an immunochemical component taken from the group consisting of antigens and antibodies in a sample, comprising:
   a vessel having the internal walls thereof covalently bound with a site-deactivating medium,
   said medium being selected from the group consisting of water soluble animal-derived plasma, animal-derived sera, vegetable-derived gelatins and mixtures thereof;
   an amount of a first immunochemical component covalently bound to said medium; and
   an amount of a second unbound immunochemical component,
   one of said first and second components being labeled,
   said first and second components being present in respective amounts sufficient to perform the assay process of claim 1.

12. The system as set forth in claim 11, said first component being an analogue of said component to be determined.

13. The system as set forth in claim 11, said label being an enzyme.

14. The system as set forth in claim 13, said enzyme being horseradish peroxidase.

15. The system as set forth in claim 13, including a color-generating agent reactive with said enzyme to generate an analytically measurable signal.

16. The system as set forth in claim 15, said antibody having an immunochemical affinity for said component to be determined.

17. The system as set forth in claim 11, said labeled component being an antibody.

18. The system as set forth in claim 11, said first component being directly covalently bound to said medium.

* * * * *